(12) United States Patent
Messerschmidt

(10) Patent No.: US 11,709,129 B2
(45) Date of Patent: Jul. 25, 2023

(54) SPECTROSCOPIC MEASUREMENTS WITH PARALLEL ARRAY DETECTOR

(71) Applicant: COR HEALTH, INC., Poway, CA (US)

(72) Inventor: Robert G. Messerschmidt, Menlo Park, CA (US)

(73) Assignee: COR HEALTH, INC., Poway, CA (US)

( * ) Notice: Subject to any disclaimer, the term of this patent is extended or adjusted under 35 U.S.C. 154(b) by 0 days.

(21) Appl. No.: 17/304,928

(22) Filed: Jun. 28, 2021

(65) Prior Publication Data

US 2021/0381958 A1    Dec. 9, 2021

Related U.S. Application Data

(60) Division of application No. 16/404,391, filed on May 6, 2019, now Pat. No. 11,079,315, which is a (Continued)

(51) Int. Cl.
*G01N 21/27* (2006.01)
*G01N 21/35* (2014.01)
(Continued)

(52) U.S. Cl.
CPC .......... *G01N 21/27* (2013.01); *A61B 5/0075* (2013.01); *A61B 5/0261* (2013.01); (Continued)

(58) Field of Classification Search
CPC .......... A61B 2562/046; A61B 5/0075; A61B 5/0261; A61B 5/145; A61B 5/14507; (Continued)

(56) References Cited

U.S. PATENT DOCUMENTS 4,514,050 A    4/1985  Stites
4,775,637 A    10/1988 Sutherland
(Continued)

FOREIGN PATENT DOCUMENTS

DE    3247355 A1    6/1984
DE    3502358 A1    7/1986
(Continued)

OTHER PUBLICATIONS

Agamatrix, Inc., Connected Health, http://agamatrix.com/products/connected-health/.

(Continued)

*Primary Examiner* — Gordon J Stock, Jr.
(74) *Attorney, Agent, or Firm* — FisherBroyles LLP; John Shimmick

(57) ABSTRACT

A measurement apparatus comprises optical components arranged to provide parallel measurements of a biological sample. The parallel sample measurements provide improved accuracy with lower detection limit thresholds. The parallel measurements may comprise one or more of Raman spectroscopy measurements or infrared spectroscopy measurements. The parallel measurements can be combined with a light source. In many embodiments, the light source comprises one or more wavelengths corresponding to resonance frequencies of one or more molecules of the sample, such as wavelengths of ultraviolet light. The wavelengths of light corresponding to resonance frequencies can provide an increased signal to noise ratio. The parallel array optical configuration can be combined with wavelengths of light corresponding to resonance frequencies in order to provide increased measurement accuracy and detection of metabolites.

10 Claims, 9 Drawing Sheets

Related U.S. Application Data continuation of application No. 14/992,945, filed on Jan. 11, 2016, now Pat. No. 10,337,984, which is a continuation of application No. PCT/US2014/047097, filed on Jul. 17, 2014.

(60) Provisional application No. 61/847,670, filed on Jul. 18, 2013.

(51) Int. Cl.

| | |
|---|---|
| *A61B 5/1455* | (2006.01) |
| *A61B 5/00* | (2006.01) |
| *A61B 5/026* | (2006.01) |
| *A61B 5/145* | (2006.01) |
| *G01N 21/33* | (2006.01) |
| *G01N 21/65* | (2006.01) |
| *G01N 33/49* | (2006.01) |
| *A61B 5/20* | (2006.01) |

(52) U.S. Cl.
CPC ........ *A61B 5/1455* (2013.01); *A61B 5/14507* (2013.01); *G01N 21/33* (2013.01); *G01N 21/35* (2013.01); *G01N 21/65* (2013.01); *G01N 33/49* (2013.01); *A61B 5/208* (2013.01); *A61B 2562/046* (2013.01); *G01N 2201/068* (2013.01); *G01N 2201/06113* (2013.01)

(58) Field of Classification Search
CPC ............ A61B 5/14532; A61B 5/14535; A61B 5/14542; A61B 5/14546; A61B 5/1455; A61B 5/14551; A61B 5/14552; A61B 5/14557; A61B 5/1459; A61B 5/208; G01N 21/27; G01N 21/33; G01N 21/35; G01N 21/3577; G01N 21/39; G01N 21/55; G01N 21/552; G01N 21/553; G01N 21/65; G01N 21/31; G01N 21/314; G01N 21/3151; G01N 2021/3144; G01N 2021/3148; G01N 2021/3155; G01N 2021/317; G01N 2021/3174; G01N 2021/3177; G01N 2201/06113; G01N 2201/068; G01N 33/49

See application file for complete search history.

(56) References Cited

U.S. PATENT DOCUMENTS

| | | | |
|---|---|---|---|
| 4,882,492 A | 11/1989 | Schlager | |
| 5,200,609 A | 4/1993 | Sting | |
| 5,280,786 A | 1/1994 | Wlodarczyk | |
| 5,288,646 A | 2/1994 | Lundsgaard | |
| 5,303,021 A | 4/1994 | Kita | |
| 5,327,777 A | 7/1994 | Kaye | |
| 5,331,958 A | 7/1994 | Oppenheimer | |
| 5,362,445 A | 11/1994 | Miyahara | |
| 5,366,903 A | 11/1994 | Lundsgaard | |
| 5,437,840 A | 8/1995 | King | |
| 5,498,324 A | 3/1996 | Yeung | |
| 5,525,518 A | 6/1996 | Lundsgaard | |
| 5,582,705 A | 12/1996 | Yeung | |
| 5,599,959 A | 2/1997 | Hosmane | |
| 5,636,640 A | 6/1997 | Staehlin | |
| 5,689,333 A | 11/1997 | Batchelder | |
| 5,706,208 A | 1/1998 | Osten | |
| 5,729,333 A * | 3/1998 | Osten ................ A61B 5/14535 356/39 |
| 5,830,133 A | 11/1998 | Osten | |
| 6,006,119 A | 12/1999 | Soller | |
| 6,141,100 A | 10/2000 | Burka | |
| 6,266,139 B1 | 7/2001 | Mannhardt | |
| 6,285,448 B1 | 9/2001 | Kuenstner | |
| 6,353,471 B1 | 3/2002 | Samsoondar | |
| 6,383,179 B1 | 5/2002 | Neuberger | |
| 6,603,987 B2 | 8/2003 | Whitson | |
| 6,614,730 B1 | 9/2003 | Vo-Dinh | |
| 6,638,769 B2 | 10/2003 | Lilja | |
| 6,676,903 B2 | 1/2004 | Potyrailo | |
| 6,788,394 B1 | 9/2004 | Garcia-Rubio | |
| 6,791,674 B2 | 9/2004 | Kawano | |
| 6,866,675 B2 | 3/2005 | Perez | |
| 6,944,487 B2 | 9/2005 | Maynard | |
| 7,001,344 B2 | 2/2006 | Freeman | |
| 7,004,928 B2 | 2/2006 | Aceti | |
| 7,087,901 B2 * | 8/2006 | Ambuel ............... G01N 21/359 250/339.01 |
| 7,150,755 B2 | 12/2006 | Levaughn | |
| 7,262,847 B2 | 8/2007 | Goodall | |
| 7,271,912 B2 | 9/2007 | Sterling | |
| 7,282,105 B1 | 10/2007 | Plunkett | |
| 7,291,497 B2 | 11/2007 | Holmes | |
| 7,299,711 B1 | 11/2007 | Linker | |
| 7,319,894 B2 | 1/2008 | Higgins | |
| 7,426,407 B2 | 9/2008 | Higgins | |
| 7,570,357 B2 | 8/2009 | Tsenkova | |
| 7,593,108 B2 | 9/2009 | Sterling | |
| 7,656,523 B2 | 2/2010 | Sun | |
| 7,787,109 B2 | 8/2010 | Dosmann | |
| 7,869,009 B2 | 1/2011 | Dosmann | |
| 7,969,307 B2 | 6/2011 | Peeters | |
| 8,033,898 B2 | 10/2011 | Mcnaughton et al. | |
| 8,041,538 B2 | 10/2011 | Meyer | |
| 8,077,042 B2 | 12/2011 | Peeters | |
| 8,160,665 B2 | 4/2012 | Mischler | |
| 8,184,273 B2 | 5/2012 | Dosmann | |
| 8,206,650 B2 | 6/2012 | Samsoondar | |
| 8,303,518 B2 | 11/2012 | Aceti | |
| 8,483,789 B2 | 7/2013 | Higgins | |
| 8,690,798 B2 | 4/2014 | Douglas | |
| 8,697,004 B2 | 4/2014 | Frazier | |
| 8,808,202 B2 | 8/2014 | Brancazio | |
| 8,821,412 B2 | 9/2014 | Gonzalez-Zugasti | |
| 8,821,413 B2 | 9/2014 | Effenhauser | |
| 8,830,449 B1 | 9/2014 | Lamego | |
| 8,900,514 B2 | 12/2014 | Forsell | |
| 9,113,836 B2 | 8/2015 | Bernstein | |
| 9,133,024 B2 | 9/2015 | Phan | |
| 9,217,706 B2 | 12/2015 | Mucci | |
| 9,259,175 B2 | 2/2016 | Stafford | |
| 9,291,504 B2 | 3/2016 | Goldring | |
| 9,341,515 B2 | 5/2016 | Schulte | |
| 9,377,396 B2 | 6/2016 | Goldring et al. | |
| 9,470,673 B2 | 10/2016 | Samsoondar | |
| 9,470,699 B2 | 10/2016 | Peeters | |
| 9,541,552 B2 * | 1/2017 | Forsell ............ G01N 33/56905 |
| 9,603,562 B2 | 3/2017 | Aceti | |
| 9,625,378 B2 | 4/2017 | Marshall | |
| 9,739,663 B2 * | 8/2017 | Haider ............... A61B 5/14552 |
| 10,052,052 B2 * | 8/2018 | Novotny ................ G01N 21/49 |
| 10,337,984 B2 | 7/2019 | Messerschmidt | |
| 10,420,498 B1 * | 9/2019 | Horstmeyer ......... A61B 5/0006 |
| 11,079,315 B2 * | 8/2021 | Messerschmidt .... A61B 5/0261 |
| 11,145,411 B2 * | 10/2021 | Treado ................... G16H 50/20 |
| 11,340,155 B2 * | 5/2022 | Messerschmidt .... G01N 33/491 |
| 2002/0122168 A1 | 9/2002 | Grcia-Rubio | |
| 2002/0123677 A1 | 9/2002 | Miki | |
| 2002/0156380 A1 | 10/2002 | Feld | |
| 2003/0018282 A1 | 1/2003 | Effenhauser | |
| 2003/0059948 A1 | 3/2003 | Hildenbrand | |
| 2003/0083686 A1 | 5/2003 | Freeman | |
| 2003/0171696 A1 | 9/2003 | Dosmann | |
| 2003/0175160 A1 | 9/2003 | Archibald | |
| 2003/0189707 A1 | 10/2003 | Naya | |
| 2003/0227628 A1 | 12/2003 | Kreimer | |
| 2004/0186359 A1 | 9/2004 | Beaudoin | |
| 2005/0033127 A1 | 2/2005 | Ciurczak | |
| 2005/0208501 A1 | 9/2005 | Goldrick | |
| 2005/0244952 A1 | 11/2005 | Cohen | |
| 2006/0043301 A1 * | 3/2006 | Mantele ............... G01N 21/552 250/339.11 |
| 2006/0055935 A1 * | 3/2006 | Cheben ..................... G01J 3/18 356/451 |

(56) References Cited

U.S. PATENT DOCUMENTS

| | | |
|---|---|---|
| 2006/0057554 A1 | 3/2006 | Watling |
| 2006/0057642 A1 | 3/2006 | Kiefer |
| 2006/0074282 A1 | 4/2006 | Ward |
| 2006/0135861 A1 | 6/2006 | Lucassen |
| 2006/0166302 A1 | 7/2006 | Clarke |
| 2007/0035818 A1* | 2/2007 | Bahatt .................... G01N 21/76 359/366 |
| 2007/0066877 A1* | 3/2007 | Arnold ................. A61B 5/0031 600/315 |
| 2007/0076208 A1 | 4/2007 | Koo |
| 2007/0134738 A1 | 6/2007 | Wells |
| 2007/0213636 A1 | 9/2007 | Kuriger |
| 2008/0138793 A1 | 6/2008 | Lindberg |
| 2008/0153171 A1 | 6/2008 | Liu |
| 2008/0218734 A1 | 9/2008 | Higashi |
| 2008/0218736 A1 | 9/2008 | Shaw |
| 2008/0300508 A1 | 12/2008 | Tomer |
| 2010/0105098 A1 | 4/2010 | Frederiske |
| 2010/0121163 A1 | 5/2010 | Vestel |
| 2010/0129919 A1 | 5/2010 | Levin |
| 2010/0142773 A1 | 6/2010 | Cha |
| 2010/0196945 A1 | 8/2010 | Forsell |
| 2010/0245803 A1 | 9/2010 | Samsoondar |
| 2010/0256524 A1 | 10/2010 | Levinson |
| 2010/0284004 A1 | 11/2010 | Reich |
| 2011/0003707 A1 | 1/2011 | Goix |
| 2011/0020849 A1 | 1/2011 | Spence |
| 2011/0105952 A1 | 5/2011 | Bernstein |
| 2011/0111435 A1 | 5/2011 | Dobson |
| 2011/0144463 A1 | 6/2011 | Pesach |
| 2011/0172508 A1 | 7/2011 | Chickering |
| 2011/0196239 A1 | 8/2011 | Behrend |
| 2011/0223654 A1 | 9/2011 | Holman |
| 2011/0278472 A1 | 11/2011 | Atzler |
| 2011/0287948 A1 | 11/2011 | Suresh |
| 2012/0016818 A1 | 1/2012 | Hackett |
| 2012/0142559 A1 | 6/2012 | Tuytten |
| 2012/0205727 A1 | 8/2012 | Kanakasabapathy |
| 2012/0257199 A1 | 10/2012 | Liu |
| 2012/0261256 A1 | 10/2012 | Chang |
| 2012/0271125 A1 | 10/2012 | Bernstein |
| 2012/0274934 A1 | 11/2012 | Messerschmidt |
| 2013/0143226 A1 | 6/2013 | Hill |
| 2013/0252237 A1* | 9/2013 | Wagner ................. G01N 21/532 435/6.1 |
| 2013/0338013 A1 | 12/2013 | Zhong |
| 2014/0112568 A1 | 4/2014 | Liu |
| 2014/0148669 A1 | 5/2014 | Saban |
| 2014/0260535 A1 | 9/2014 | Mcgill |
| 2014/0336534 A1 | 11/2014 | Balligand |
| 2014/0336536 A1 | 11/2014 | Brancazio |
| 2015/0055121 A1 | 2/2015 | Forsell |
| 2015/0057530 A1 | 2/2015 | Roggeveen |
| 2015/0087944 A1 | 3/2015 | Levinson |
| 2015/0208985 A1 | 7/2015 | Huang |
| 2015/0338338 A1 | 11/2015 | Messerschmidt |
| 2016/0025624 A1 | 1/2016 | Mucci |
| 2016/0029937 A1 | 2/2016 | Sia |
| 2016/0058354 A1 | 3/2016 | Phan |
| 2016/0066828 A1 | 3/2016 | Phan |
| 2016/0123869 A1 | 5/2016 | Messerschmidt |
| 2016/0151569 A1 | 6/2016 | Stafford |
| 2016/0252453 A1 | 9/2016 | Lewis |
| 2016/0302707 A1 | 10/2016 | Pesach |
| 2017/0010154 A1 | 1/2017 | Spudich |
| 2017/0127990 A1 | 5/2017 | Levinson |
| 2017/0350814 A1 | 12/2017 | Messerschmidt |
| 2018/0136193 A1 | 5/2018 | Messerschmidt |
| 2022/0330828 A1* | 10/2022 | Popp ..................... A61B 5/1455 |

FOREIGN PATENT DOCUMENTS

| | | |
|---|---|---|
| EP | 0476192 | 3/1992 |
| EP | 2700933 | 2/2014 |
| EP | 3282937 A1 | 2/2018 |
| GB | 740181 A | 11/1955 |
| JP | 2002131319 | 5/2002 |
| WO | 1986000513 | 1/1986 |
| WO | 02058556 | 8/2002 |
| WO | 03055379 A2 | 7/2003 |
| WO | 2005080946 | 9/2005 |
| WO | 2009117416 | 9/2009 |
| WO | 2011153271 A1 | 12/2011 |
| WO | 2013058084 | 4/2013 |
| WO | 2013134786 A2 | 9/2013 |
| WO | 2013155458 A1 | 10/2013 |
| WO | 2013156806 A2 | 10/2013 |
| WO | 2013180652 A1 | 12/2013 |
| WO | 2013186628 | 12/2013 |
| WO | 2014191980 | 12/2014 |
| WO | 2015009970 A1 | 1/2015 |
| WO | 2015112919 | 7/2015 |
| WO | 2015131151 A2 | 9/2015 |
| WO | 2015166237 A1 | 11/2015 |
| WO | 2015179288 A1 | 11/2015 |
| WO | 2015179969 | 12/2015 |
| WO | 2016086071 A1 | 6/2016 |
| WO | 2016168090 A1 | 10/2016 |
| WO | 2017165403 A1 | 9/2017 |
| WO | 2018085699 A1 | 5/2018 |

OTHER PUBLICATIONS

Alam, "Measurement of pH in Whole Blood by Near-Infrared Spectroscopy", Applied Spectroscopy, Mar. 1, 1999, pp. 316-324, vol. 53, issue 3—Abstract.

Bo, "Capillary method for measuring near-infrared spectra of microlitre volume liquids", Journal of Zhejiang University—3CIENCE A, Feb. 1, 2007, pp. 171-175, vol. 8, Issue 2—Abstract.

Domjan, "Rapid Analysis of Whole Blood and Blood Serum Using near Infrared Spectroscopy", Journal of Near Infrared Spectroscopy, Mar. 1, 1994, pp. 67-78, vol. 2, Issue 2—Abstract.

Eigenvector Research Incorporated website. Accessed Apr. 30, 2015. http://www.eigenvector.com/software/solo.htm.

Engel, "Seventh Sense Biosystems Sucks In $10M for Simple Blood-Draw Device", Xconomy Boston, Nov. 18, 2016, http://www.xconomy.com/boston/2016/11/18/seventh-sense-biosystems-sucks-in-10m-for-simple-blood-draw-device/#.

Gentag, NFC and Optical Skin Patches, http://gentag.com/nfc-skin-patches/.

Giardina et al., "The Multiple Functions of Hemoglobin", Critical Reviews in Biochemistry and Molecular Biology, (Mar. 1, 1995), vol. 30, pp. 165-196, XP 055498007.

Huang, "Optimal waveband and mathematical model for analysis of human whole blood glucose by near infrared transmission spectroscopy", 5th International Symposium on Advanced Optical Manufacturing and Testing Technologies, Oct. 11, 2010, Dalian, China—Abstract.

International preliminary report on patentability dated Jan. 28, 2016 for PCT Application No. US2014/047097.

International search report and written opinion dated Nov. 6, 2014 for PCT Application No. US2014/047097.

Kim, "Prediction of glucose in whole blood by near-infrared spectroscopy: Influence of wavelength region, preprocessing, and hemoglobin concentration", Journal of Biomedical Optics, Jul. 1, 2006, 11(4), 041128—Abstract.

Lafrance, "Measurement of lactate in whole human blood with near-infrared transmission spectroscopy", Talanta, Jul. 4, 2003, pp. 635-641, vol. 60, Issue 4, Elsevier—Abstract.

Lakshmi et al., "A simple slide test to assess erythrocyte aggregation in acute ST-elevated myocardial infarction and acute ischemic stroke: Its prognostic significance", Journal of Pathology and Microbiology, (Jan. 1, 2011), vol. 54, pp. 63-69, XP009507350.

Liu et al. "Application of a Genetic Algorithm to Quantitative Analysis of Overlapped FTIR Spectra", Spectroscopy Letters, vol. 34, No. 1, Jan. 22, 2001.

MDPI, Diagnostics—Open Access Journal of Medical Diagnosis, https://www.mdpi.com/journal/diagnostics/.

(56) References Cited

OTHER PUBLICATIONS

Murayama, "Near-infrared spectroscopy for liquids of microliter volume using capillaries with wall transmission", Analyst, 2003, Issue 7—Abstract.

Nemaura Medical, Improve blood sugar management, http://www.nemauramedical.com/sugarbeat/.

Rosenfeld, "New Skin Patch Monitors Glucose and Delivers Diabetes Drugs", Mar. 8, 2017, http://mentalfloss.com/article/93063/new-skin-patch-monitors-glucose-and-delivers-diabetes-drugs.

Staniszewska-Slezak et al. "Plasma biomarkers of pulmonary hypertension identified by Fourier transform infrared spectroscopy and principal component analysis", The Analyst, vol. 140, No. 7, Jan. 1, 2015.

Sund et al. "Cell Membrane Orientation Visualized by Polarized Total Internal Reflection by polarized total internal reflection fluorescence," Biophysical Journal, vol. 77, Issue 4, Oct. 1999, pp. 2266-2283.

Turza, "Near Infrared Analysis of Whole Blood and Plasma in Blood—Collecting Tubes", Journal of Near Infrared Spectroscopy, Jun. 1, 2006, pp. 147-153, vol. 14, issue 3—Abstract.

Wan X, "Identification of Animal Whole Blood Based on Near Infrared Transmission Spectroscopy", PubMed, Guang Pu Xue Yu Guang Pu Fen Xi. Jan. 2016; 36(1):80-3. Chinese—Abstract.

\* cited by examiner

SPECTROSCOPIC MEASUREMENTS WITH PARALLEL ARRAY DETECTOR

CROSS-REFERENCE

This application is a divisional of U.S. patent application Ser. No. 16/404,391, filed May 6, 2019, now U.S. Pat. No. 11,079,315, issued Aug. 3, 2021, which is a continuation of U.S. patent application Ser. No. 14/992,945, filed Jan. 11, 2016, now U.S. Pat. No. 10,337,984, issued Jul. 2, 2019, which is a continuation of International Patent Application No. PCT/US2014/047097, filed Jul. 17, 2014, published as WO 2015/009970 on Jan. 22, 2015, which claims priority to U.S. Patent Application No. 61/847,670, filed Jul. 18, 2013, entitled "Spectroscopic Measurement of Metabolites with Parallel Array Detector", the entire disclosures of which are incorporated herein by reference.

BACKGROUND

The field of the present invention is related to the measurement of biological samples.

Prior methods and apparatus of measuring metabolites are less than ideal. Although the prior methods and apparatus can be used to determine amounts of metabolites in patients, in many instances the required sample size is larger than ideal. For example, metabolic panels, toxicology screens and other tests can require removal of more blood from the patient than would be ideal. Also, the cost and complexity of the measurement apparatus can be greater than would be ideal such that fewer patients are measured than would be ideal in at least some instances. Although in home monitoring can be used, the invasiveness and discomfort of pricks with sharp objects and other inconveniences can result in less than ideal user satisfaction. Also, the fluid measured at locations away from the fingertips may comprise interstitial fluid that can have amounts of metabolites that differ from blood amounts in at least some instances.

Although Raman spectroscopy has been proposed to measure biological samples, the prior methods and apparatus provide less than ideal measurements in at least some instances. For example, Raman spectroscopy relies on light scatter and the signal to noise ratio and sample measurement duration can be less than ideal with the prior Raman spectroscopy methods and apparatus. Also, biological samples can degrade, and the prior methods and apparatus can provide less than ideal amounts of sample degradation and may not adequately address degradation of biological samples in at least some instances.

In light of the above, it would be beneficial to provide improved methods and apparatus of measuring biological samples. Ideally such methods and apparatus would provide lower detection limits of metabolites in samples, decreased invasiveness and discomfort, decreased complexity, increased accuracy and decreased cost.

SUMMARY

Embodiments of the present invention provide improved methods and apparatus for measuring samples such as biological samples. In many embodiments, a measurement apparatus comprises optical components arranged to provide parallel measurements of the biological sample. The parallel sample measurements can provide improved accuracy with lower detection limit thresholds. The parallel measurements may comprise one or more of Raman spectroscopy measurements or infrared spectroscopy measurements. The parallel measurements can be combined with a light source such as a near infrared or ultraviolet light source. In many embodiments, the light source comprises one or more wavelengths corresponding to resonance frequencies of one or more molecules of the sample, such as wavelengths of ultraviolet light. The wavelengths of light corresponding to resonance frequencies can provide an increased signal to noise ratio. The parallel array optical configuration can be combined with wavelengths of light corresponding to resonance frequencies in order to provide increased measurement accuracy and detection of metabolites. In many embodiments, an area array detector comprises a plurality of rows and plurality of columns of sample detectors such as pixels sensitive to the light transmitted from the sample. The area array detector can be configured to receive a spectroscopic signal from a sample such as a biological sample. The biological sample may comprise a bodily fluid such as one or more of blood, urine, saliva, blood cells, blood plasma, or interstitial fluid, for example.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION

Figure 1A:
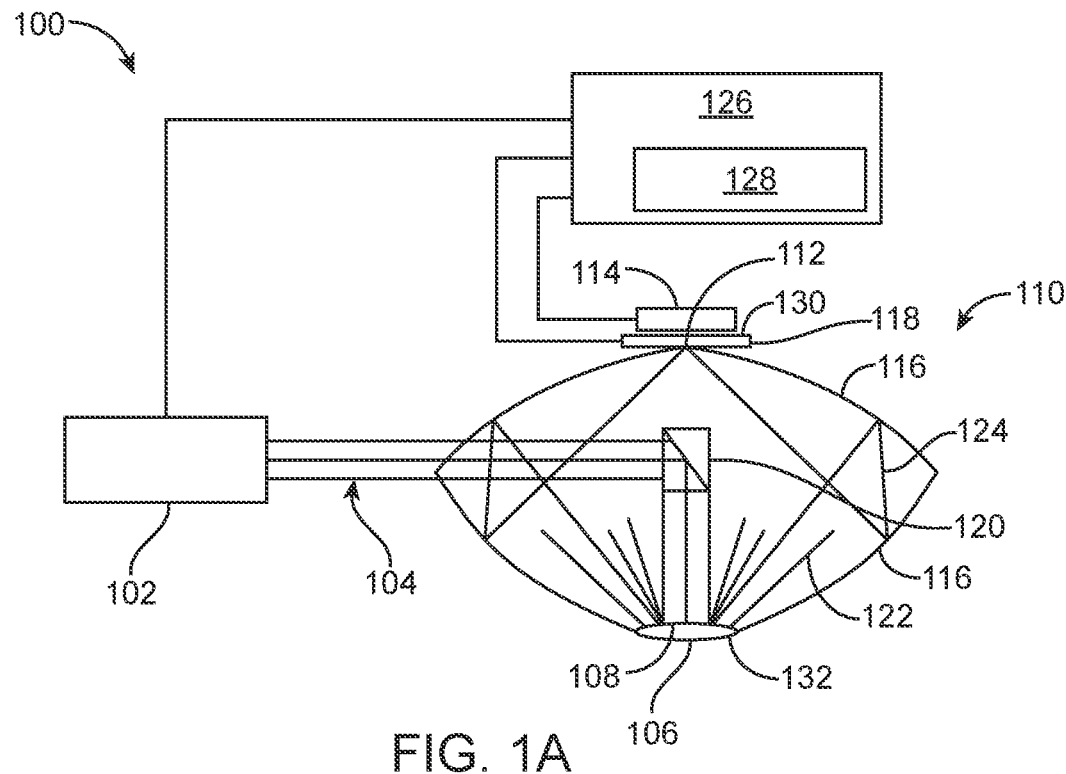
FIG. 1A shows an apparatus to measure a plurality of spectra of a sample in parallel, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the disclosure as described herein.

As used herein like characters identify like elements.

The embodiments as described herein can provide in vitro diagnostics of the patient, and the sample may comprise a specimen of one or more of tears, saliva or urine. The sample may comprise blood, for example. In many embodiments, a plurality of samples from the patient can be measured, for example, tears of the patient, saliva of the patient and urine of the patient. The patient can provide these measurements of himself or herself, for example. Alternatively or in combination, these samples can be measured by a health care provider such as laboratory service providing a metabolic panel to the patient.

The embodiments disclosed herein can be combined in one or more of many ways to provide improved measurements of patient samples.

Embodiments as described herein can be combined with one or more of many prior methods and apparatus of obtaining samples from patients. For example, the sample of the patient or subject may comprise a sample of urine, blood, saliva, tissue or other sample of the patient obtained with one or more of many prior methods and apparatus such as needles, catheters, and swabs.

The embodiments as described herein provide improved measurements that can allow in many embodiments described volumes of the sample taken from the patient. For example, in order to measure the blood of the patient, the volume of blood removed from the patient can be decreased substantially. For example, in order to obtain a metabolic panel and toxicology panel of the patient, the amount of blood can be substantially decreased due to the improved signal to noise ratio. The parallel arrays as described herein can be used to decrease the amount of noise and increase the signal to noise ratio substantially. For example, the parallel measurement array configuration can provide an improved signal to noise ratio of approximately three orders of magnitude and a factor of one thousand for example. Alternatively or in combination, the embodiments as described herein can provide improved tuning of the frequencies of light transmitted to the sample for measurement. For example, the tuned wavelengths may correspond to ultraviolet wavelengths and the wavelengths of light can provide an additional improvement of the signal to noise ratio, for example, a three order of magnitude improvement or an additional factor of 1,000. The embodiments as described herein can provide substantially improved measurements of biological samples from the patient with substantially increased accuracy and decreased sample volumes. Work in relation to embodiment suggests that the patient may undergo substantially less discomfort with the present apparatus than the prior devices and that the accuracy of the measurements can be substantially improved so as to provide improved diagnostics and treatment of the patient. Work in relation to embodiments suggests that metabolites can be measured at part per billion amounts and even the part per trillion amounts depending upon the metabolite and embodiments used.

Work in relation to embodiments suggests that providing decreased sample volumes such as decreased blood volume can decrease the amount of pain and/or discomfort a subject may undergo during testing. In many embodiments, the sample comprises a layer of material of the patient adsorbed on the surface of the sharp object, such that the volume can be decreased substantially. For example, a sharp object such as a blade can provide a sample on the surface of the substrate and imaging the sample can provide accurate measurements of the metabolites as described herein from the decreased sample size. In some embodiments, an individual blood cell can be measured on the area array, such as the CCD array, and the spectra of the individual blood cell measured, for example. Alternatively or in combination, other fluids of the sample can be measured, such as fluids of a hematocrit, for example. For example, blood plasma can be located on the surface of the sharp object in combination with blood cells and the spectra of the sample determined as described herein. Although the blood sample is described, other samples of the patient can be measured, such as saliva, urine, for example.

FIG. 1A shows an apparatus 100 to measure a sample in accordance with embodiments. The apparatus comprises a laser 102 to provide a measurement beam 104 and support 106 configured to receive a sample 108. The apparatus comprises imaging optics 110 to form an image 112 of the sample on a detector array 114 such as a CCD array, when the sample has been placed on the support. The imaging optics may comprise a first curved reflector 116 and a second curved reflector, for example. Alternatively or in combination, the imaging optics may comprise one or more lenses 118 to image the sample onto the CCD array. The laser beam extends along an optical path from the laser source to the sample. A beam splitter (hereinafter "BS") 120 is located along the optical path. The laser beam is directed from the beam splitter to the sample along the optical path.

In many embodiments the apparatus is configured to measure Raman light scattering. Alternatively or in combination, the apparatus can be configured to measure infrared absorbance spectroscopy, for example. In many embodiments, light 122 scattered from the sample is directed away from the beam splitter toward a first curved reflector, and the light ray 124 reflected from the first curved reflector is reflected toward a second curved reflector toward the sensor array so as to form an image on the sensor array, which may comprise a CCD array.

Light scattered from the sample can be imaged onto the CCD array. The CCD array is coupled to a processor 126. The processor comprises circuitry to process signals from the CCD array, and may comprise a processor commercially available from Intel, Motorola, or Texas Instruments, for example. Alternatively or in combination, the processor may comprise logic gate array circuitry, such as a programmable gate array logic circuitry (hereinafter "PAL"), for example. The processor comprises a tangible medium 128 embodying instructions of a computer readable program. The tangible medium may comprise memory of a computer such as read only memory, random access memory and many forms of computer memory known to a person of ordinary skill in the art. The processor may comprise a computer and a display, for example. The processor may comprise an input display such as a touch screen display and communication circuitry coupled to the CCD array in wireless communication to transmit data. In many embodiments the processor comprises one or more of many components of a smart phone such as an Apple iPhone or a smart phone running the Android™ operating system such as a Samsung Galaxy™ smart phone, for example.

In many embodiments the laser and optics are configured to provide improved sampling. For example, a homogenizer can be placed in the laser beam so as to provide a substantially uniform intensity profile on the sample surface. The substantially uniform energy profile can comprise an energy intensity constant to within about +/−25% of the average value across the sample surface. The laser may comprise a laser configured to provide the substantially uniform intensity beam profile or alternatively the laser can be directed to a beam homogenizer such as a plurality of prisms, a plurality of lenses, a detractive optic or other beam homogenizing structure so as to provide a substantially uniform beam to the sample. The light from the sample is imaged onto the CCD array. The image of the sample is formed on or near the surface of the CCD array in order to provide additional information.

In many embodiments, a filter 130 is provided in front of the CCD array in order to filter light transmitted to the CCD array and determine a spectrum of the light energy scattered from the sample. The filter may comprise one or more of an optically transmissive filter, an optically reflective filter, or a grating having an angle oriented to selectively pass wavelengths of light, for example.

In many embodiments, a heat sink 132 is provided to conduct heat away from the sample when the laser beam as described herein impinges the sample in order to avoid and inhibit degradation of the sample.

The laser can be figured in one or more of many ways to provide a measurement beam. The laser may comprise a beam in the ultraviolet, infrared or near infrared or infrared, for example. The measurement beam may comprise a laser beam having a wavelength of approximately 785 nanometers, for example. Alternatively or in combination, the laser may comprise an ultraviolet beam having a wavelength of approximately 224 nanometers, for example.

In many embodiments, the laser beam is tuned to a wavelength corresponding to resonance of the molecular bonds of the sample in order to provide an enhanced signal. Work in relation to embodiments suggest that ultraviolet wavelengths within a range from about 200 to 250 nanometers can provide resonance of the sample so as to provide an enhanced signal. The UV wavelength of the laser beam can be identified and provided in order to provide decreased fluorescence of the sample and a substantially greater Raman Signal. For example, a wavelength from about 220 to about 230 nanometers can be provided. Work in relation to embodiment suggest that UV laser beams having an appropriate wavelength can increase the signal to noise ratio by approximately three orders of magnitude (a factor of 1000). The laser may comprise a helium argon laser emitting a wavelength of approximately 224.3 nanometers, for example. A laser may comprise a hollow cathode laser tube, for example. Alternatively or in combination, the laser beam may comprise a frequency-doubled or frequency-mixed laser beam and combinations thereof, for example.

In many embodiments the laser comprises a solid state laser diode having a near infrared wavelength within a range from about 780 to about 790 nanometers for example 785 nanometers. The output of such a laser can be within a range from about 850 to 930 nanometers, for example. The output Raman scattered light can be measured with a detector as described herein. Based on the teachings provided herein a person of ordinary skill in the art can identify a commercially available detector array such as a CCD array capable of measuring the wavelengths of the Raman signal. For example, for Raman scatter output having wavelengths from about 850 to 930 nanometers a CCD array can be used to measure the wavelengths. For the UV laser beam a CCD array can be identified by a person of ordinary skill in the art capable of measuring ultraviolet Raman scattering having wavelengths corresponding to wave numbers from about 800 to 1600 inverse centimeters, corresponding to wavelengths within a range from about 229-234 nm, for example. The Raman scattering can be measured with a plurality of filters as described herein, for example.

In many embodiments the apparatus comprises a wavelength selector such as an optical filter, grating or other structure to separate wavelengths of light in order to determine the intensity of specific wavelengths of light.

Figure 1B:
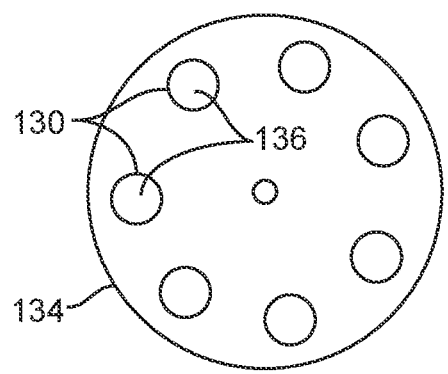
FIG. 1B shows a filter wheel, in accordance with the apparatus of FIG. 1A.

FIG. 1B shows a filter wheel 134 in accordance with embodiments. The filter wheel comprises a plurality of filters 130 located in a plurality of apertures 136. The filter wheel can be coupled with a processor in order to place a filter in front of the CCD array for measurement of the optical signal. The plurality of filters may comprise filters having wavelengths within a range from about 850 to 930 nanometers for example. Alternatively or in combination the filters can be configured to transmit wavelengths within a range from about 229 to 234 nanometers for example. The filter wheel may comprise a component of a commercially available apparatus for example. A commercially available camera suitable for incorporation in accordance with embodiments may comprise a spectral cam commercially available from Pixelteq.com. The multispectral wheel camera can be provided with filters in accordance with the teachings described herein, in order to provide appropriate resolution from about 229 to 234 nanometers for example. The filter wheel can be under control of the processor and the laser can be used in combination with the filter wheel to irradiate the sample when one or more of the filters is in an appropriate position in order to measure the sample. The filter wheel comprises a plurality of filters and each of the plurality of filters is configured to pass specific wavelengths in order to measure the sample. For example, the filter wheel can be provided with six filters, each filter configured to pass approximately one nanometer of bandwidth within a range from about 229 to 234 nanometers. For example, a first filter can transmit light having wavelengths of approximately 229-230 nanometers. A second filter can be configured to transmit light having wavelengths of approximately 230-231 nanometers. A third filter can be provided configured to transmit light having wavelengths of approximately 231-232 nanometers and a sixth filter can be provided to transmit light having wavelengths of approximately 234-235 nanometers for example.

Figure 1C:
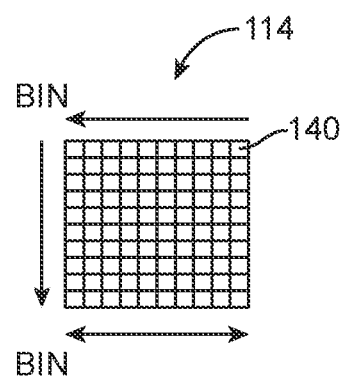
FIG. 1C shows an area detector array in accordance with the apparatus of FIG. 1A.
Figure 1D:
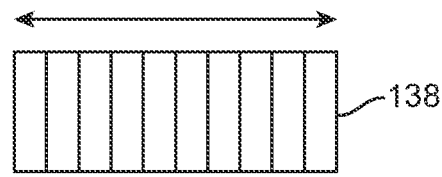
FIG. 1D shows a linear variable filter, in accordance with embodiments.

FIG. 1D shows a linear variable filter 138 in accordance with embodiments which may comprise a slidable filter in configured to provide a plurality of filters similar to the filter wheel. Alternatively or in combination the linear variable filter may comprise a gradual gradation of wavelengths transmitted in order to provide measurement of the samples described herein.

The filter wheel may comprise a plurality of filters configured to measure near infrared light in accordance with embodiments. For example, the illumination laser beam may comprise wavelengths within a range from about 780 to 900 nanometers, for example, 785 nanometers is described herein. In many embodiments, the laser comprises a gallium aluminum arsenide (GaAlAs) diode laser beam. The 785 nanometer laser beam can be substantially collimated and directed to the sample as described herein, for example.

The laser beam directed to the sample can be configured in one or more of many ways as described herein. For example, the laser beam can be substantially collimated and directed toward the sample with the beam splitter such that the laser beam is substantially reflected from the beam splitter toward the sample, and the laser beam reflected from the sample is reflected from the beam splitter toward the laser beam. Alternatively or in combination, the laser beam can be slightly convergent or slightly divergent as directed to the sample.

FIG. 1C shows a parallel sensor array 114 and parallel optical configuration for parallel measurements in accordance with many embodiments. The sensor array comprises an N by M sensor array such as a CCD array comprising a plurality of N rows and a plurality of M columns, wherein N and M are integers. For example, the sensor array may comprise a thousand rows and a thousand columns, so as to provide approximately one million pixel elements. Each pixel element 140 may comprise a detector as described herein. The exact number of pixels will depend upon the specific detector employed in accordance with embodiments. For example, the sensor array may comprise 3,000 columns and 3,000 rows so as to provide 9,000,000 pixels. For example, the range of the number of pixels of the sensor array can be within a range from about 1,000,000 (one million) pixels to about 10,000,000 (10 million) pixels, for example. A person of ordinary skill in the art will recognize many variations in accordance with the embodiments described herein and the CCD array may comprise fewer than 1,000,000 pixels or more than 10,000,000 pixels.

The intensity can be measured when the filter has been placed in front of the CCD array to select specific wavelengths of light in order to measure a plurality of spectra in parallel. For example, a filter having a one nanometer bandwidth can be placed along the optical path in front of the pixels of the CCD array to measure over 1,000,000 pixels, for example. The intensity can be measured for each of the pixels for each of the plurality of filters in order to measure the spectra in parallel, for example.

In many embodiments, the signal to noise ratio improves approximately as the square root of the number of samples, for example, providing 1,000,000 detectors will provide a signal to noise ratio improvement of approximately 1,000 over a single detector, for example. The parallel measurement array as described herein can provide a signal to noise ratio improvement of approximately 1,000 over a single channel measurement apparatus.

The sample can be placed on the support in one or more of many configurations. For example, the thickness of the sample can be irregular. Alternatively or in combination, the sample can be substantially uniformly spread on the sample area of the support with a thickness of that is uniform to approximately +/−25% (percent) of an average value in order to provide a substantially uniform sample profile.

The parallel array measurement configuration can be combined with the substantially uniform laser beam intensity profiles described herein. Alternatively or in combination the parallel array configuration can be combined with the ultraviolet measurement beam as described herein.

The wavelength selector comprising the one or more filters can be figured in one or more of many ways as described herein. For example, with near infrared embodiments, the filter wheel may comprise eight filters having approximately ten nanometer bandwidth from 850 to 930 nanometers, for example. A first filter may have a bandwidth from about 850 to 860 nanometers. A second filter may have a bandwidth from approximately 860 to 870 nanometers. The eighth filter may comprise a bandwidth from approximately 920 to 930 nanometers, for example. The filter wheel can be rotated to transmit the selected wavelengths of light. The number of filters can be determined in order to provide an approximate signal and the numbers provided herein provide examples in accordance with embodiments. For example, the filter wheel may comprise from 5 to 100 filters, or more or fewer filters, for example.

The measurement sample which may comprise a specimen of a patient can be configured in one or more of many ways to provide additional information suitable for use in combination with the optical measurements as described herein. For example, the sample can be allowed to dry and a plurality of parallel measurements obtained over time so as to measure a time profile of the spectra of the sample. Further, as the sample can be imaged onto the sensor array, a spatially resolved drying profile of the sample can be obtained over time. For example, a drop of blood can be placed on the sample substrate in order to provide a blood drop irradiated with the laser beam and imaged onto the sensor array. The blood drop can be thicker centrally and thinner peripherally or substantially uniform. The outer portion of the sample can dry faster than the inner portion to provide a spatially resolved drying profile over time. The spatially resolved drying profile can be resolved both temporally and spatially in order to provide an improved profile of the beam and improved profile of the spectrum. The improved profile of the spectrum may comprise a multi-dimensional fingerprint suitable for identifying metabolites as described herein. Alternatively or in combination, the sample can be actively heated, for example, with a heating device or with a laser beam, for example, and the heating of the sample can provide additional information with respect to the sample. In many embodiments the sample can be stretched, for example with a stretchable substrate such that the stretching of the sample can provide additional information.

In many embodiments, a chromatography plate can be provided as the surface of the support that receives the sample in order to spatially resolve and perform chromatography on the sample with one or more of Raman or infrared spectroscopy as described herein. For example, the sample can separate when placed on the chromatography plate and the separation of the sample provided by the chromatography can provide an optical signal that is sensitive to the separation of the sample on the chromatography surface. The chromatography surface may comprise a substrate configured for thin layer chromatography (hereinafter "TLC"), for example. The separation of sample on the plate can be measured spatially with imaging and temporally with a plurality of samples at predetermined times, such that the Raman spectroscopy can be measured and with the spatial and temporal profile in order to identify and measure amounts of the metabolites of the sample.

An acoustic profile can be provided with the measurement beam so as to separate the sample into rings with vibration. For example, rings corresponding to resonant modes of the sample such as a blood drop work in relation to embodiment suggests that such acoustic profiling of the beam can provide additional information of the sample.

Figure 2A:
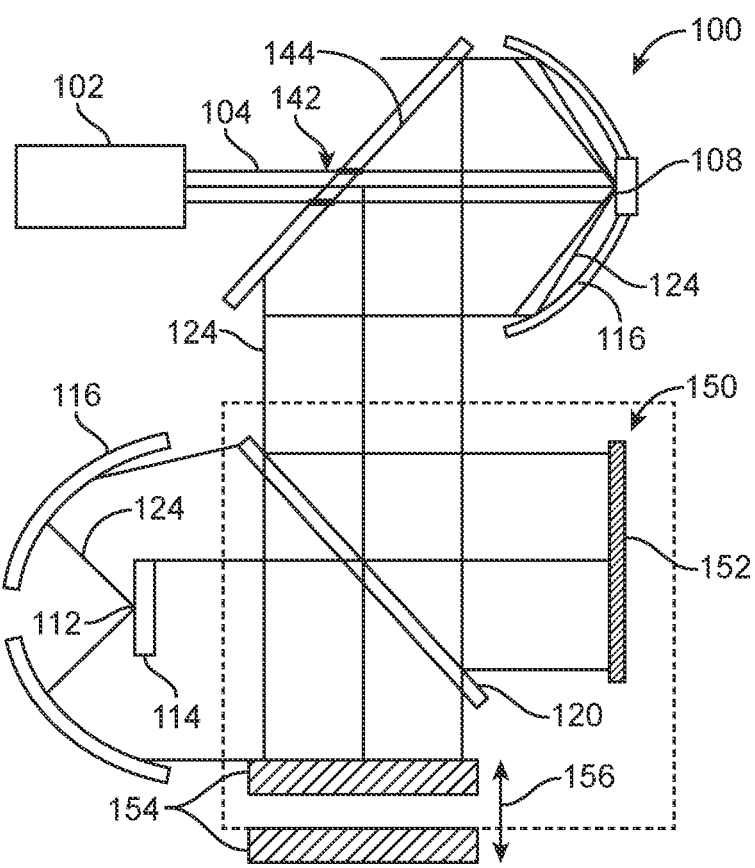
FIG. 2A shows an apparatus to measure a plurality of spectra of a sample in parallel with an interferometer, in accordance with embodiments.

FIG. 2A shows a measurement apparatus 100 in accordance with embodiments. The measurement apparatus comprises many components similar to the apparatus 100 of FIG. 1A. The apparatus comprises a laser 102 configured to emit a laser beam 104. The laser beam can be collimated, convergent or divergent, as described herein for example. The laser beam is directed through an aperture 142 of a mirror 144 toward the specimen sample 108. The laser beam impinges upon the sample, and the sample provides a plurality of light rays 124 that are transmitted away from the sample. The light rays transmitted away from the sample may comprise Raman scattered light rays, infrared light rays transmitted through the sample, or other light rays as described herein, for example.

The light rays which are scattered can be imaged with a curved reflector 116 as described herein. The curved reflector may comprise a spherical reflector, parabolic reflector or other reflector arranged to collect light rays.

The light rays reflected off the reflector can be directed in a generally parallel configuration toward the interferometer 150. An interferometer can be provided with the measurement apparatus in order to determine an interference signal of the sample of the light rays emitted from the sample. This interferometric signal can provide a spatial frequency distribution as described herein. Light rays reflected from the curved reflector are directed toward the mirror having the aperture formed therein and the light rays are directed away from the aperture and directed into the interferometer with the mirror.

The light rays directed into the interferometer are directed to a first leg of the interferometer and a second leg of the interferometer. In many embodiments, the interferometer comprises one or more components of a Michelson interferometer. The interferometer comprises a beam splitter 120 and the beam splitter directs light along the first leg of the interferometer toward a fixed reference mirror 152. The beam splitter transmits a second portion of the light to a movable mirror 154 that moves from a first position to a second position with a plurality of locations in between so as to measure a plurality of interference signals. The displacement of the movable mirror is shown with an arrow 156 and the movable mirror along the second leg of the interferometer is moved so as to provide interference at the CCD array 114 upon which the sample is imaged. The movable mirror is placed at a plurality of positions to change the optical path length along the measurement leg. The optical signal of each of the plurality of detectors is measured at each position of the movable mirror.

A second curved reflector 116 is provided in proximity to the CCD array and the second curved reflector may comprise a spherical or parabolic reflector with the CCD array located at a location corresponding to an image 112 of the light from the specimen. The optical image directed onto the CCD array is measure for each of the plurality of mirror positions with a processor as described herein.

The light from the reference leg and movable mirror leg are combined with the beam splitter in order to provide an interference signal on the CCD array. Light from the fixed reference mirror is directed toward the CCD array and light from the movable mirror is directed toward the CCD array, such that the light signals interfere when they arrive at the CCD array.

Figure 2B:
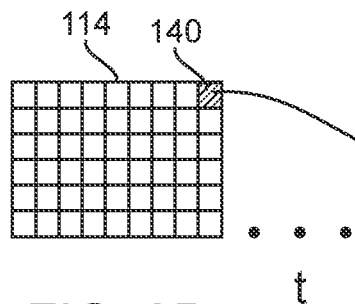
FIG. 2B shows an area array detector in accordance with the apparatus of FIG. 2A.

FIG. 2B shows a CCD sensor array 114 and a pixel 140 of the CCD sensor array in accordance with embodiments. The CCD array comprises a sensor array as described herein. Each of the pixels in the sensor array can be measured as described herein and a time profile provided. The CCD array may comprise approximately 1,000,000 or more pixels, for example, so as to improve the signal to noise ratio as described herein.

Figure 2C:
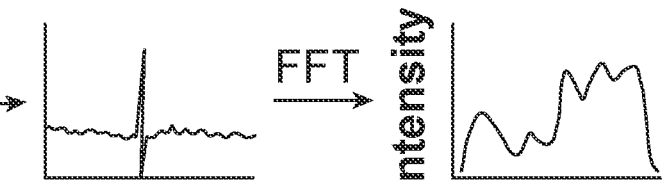
FIG. 2C shows a signal of an element of an area array detector in accordance with FIGS. 2A and 2B, in accordance with embodiments.

FIG. 2C shows a time profile over time measured with the pixels of the CCD array. The time profile corresponds to locations of the movable mirror such that each time shown in FIG. 2C corresponds to a location of the movable mirror, and the movable mirror can be moved to a plurality of discrete locations and the interference signal measured at each of the plurality of discrete locations so as to provide the interference profile shown in FIG. 2C.

Figure 2D:
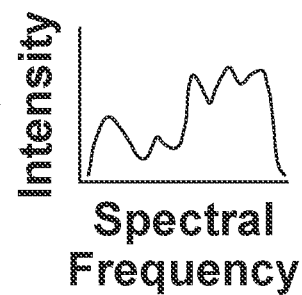
FIG. 2D shows a spectral frequency intensity distribution profile of a plurality of wavelengths of light in accordance with FIGS. 2A, 2B and 2C.

FIG. 2D shows a spatial frequency intensity distribution of the interference signal of FIG. 2C by taking the fast Fourier transform (hereinafter "FFT") or other transform of the intensity profile of FIG. 2C. The spectral frequency intensity profile distribution can be determined as shown in FIG. 2D. The spectral frequency distribution as shown in FIG. 2D can be combined so as to provide an improved signal to noise ratio.

While the data of the sensor array can be combined in one or more of many ways, work in relation to embodiment suggests that obtaining a Fourier transform of each of the data of each pixel and then combining the spectral frequency to provide a improved signal to noise ratio. Alternatively, the intensity of each of the pixels can be combined for each mirror position prior to obtaining the fast Fourier transform as shown in FIG. 2D. A person of ordinary skill in the art will recognize many variations in accordance with the teachings disclosed herein.

Figure 2E:
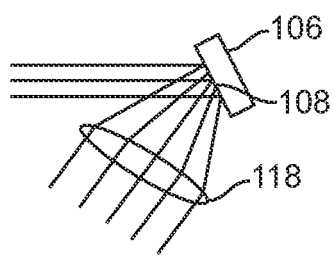
FIG. 2E shows a lens to measure a sample, in accordance with embodiments.

FIG. 2E shows an imaging apparatus suitable for use with an interferometer as described herein. A sample 108 can be provided on the substrate 106 and scatter from the sample can be measured with the lens 118. The lens can be positioned at approximately the focal distance of the lens from the sample such that the light transmitted from the lens comprises substantially collimated light suitable for use with the interferometer as described herein with reference to FIG. 2A, for example. Although a bi-curved geometric lens is shown, a curved mirror can be provided, for example, and the lens may comprise one or more of many lenses, such as a Fresnel lens, a diffractive lens, or other lens, for example.

Figure 3A:
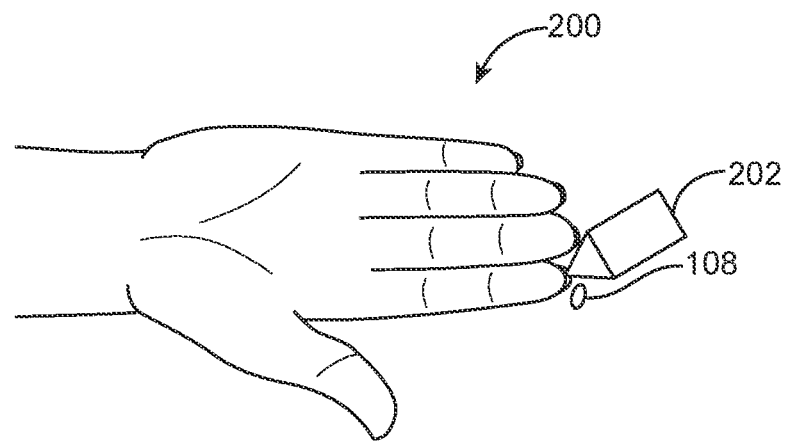
FIG. 3A shows a sample provided by a hand of a subject with a sharp substrate pricking the subject.

FIG. 3A shows measurement of a sample in accordance with embodiments. A subject, such as a patient, provides a hand 200 and the hand is contacted with a sharp object 202, such as a diamond blade or a metal substrate, in order to prick the hand obtain the sample 108. The sharp object such as the diamond blade or metal substrate can be removed from the skin of the subject, and the sample measured with the apparatus as described herein. For example, light can be transmitted through the sample when the sample comprises an optically transmissive structure such as the diamond blade. Alternatively, light can be reflected from the surface of non-optically transmissive substrate such as the metal substrate in order to measure the sample.

Figure 3B:
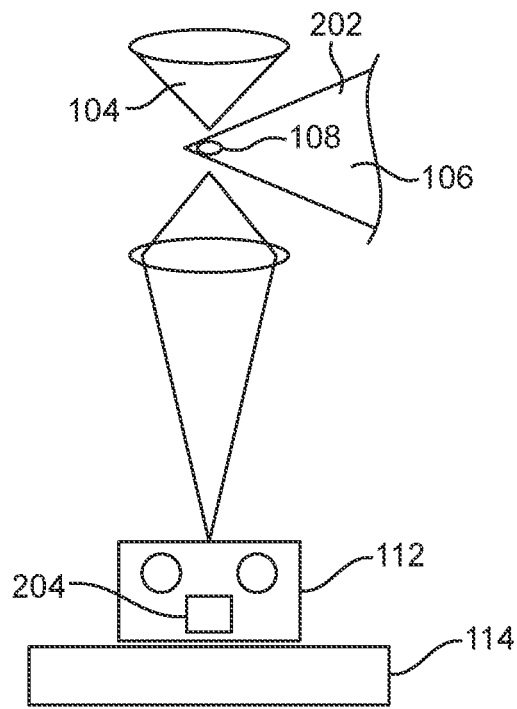
FIG. 3B shows an image of the sample supported with the sharp substrate as in FIG. 3A in order to measure metabolites of the subject in accordance with embodiments.

In many embodiments, the sample 108 is imaged onto an area array 114 such as the CCD array as shown schematically in FIG. 3B. FIG. 3B shows an image 112, a schematic of an image shown on a CCD array with a region having an analyte 204 to be analyzed shown on the image of the CCD array. The use of the microscope combined with the measurement apparatus as described herein in order to image the sample with the CCD array as described herein can provide improved accuracy of measurements with decreased volume of the sample obtained from the subject.

Figure 4A:
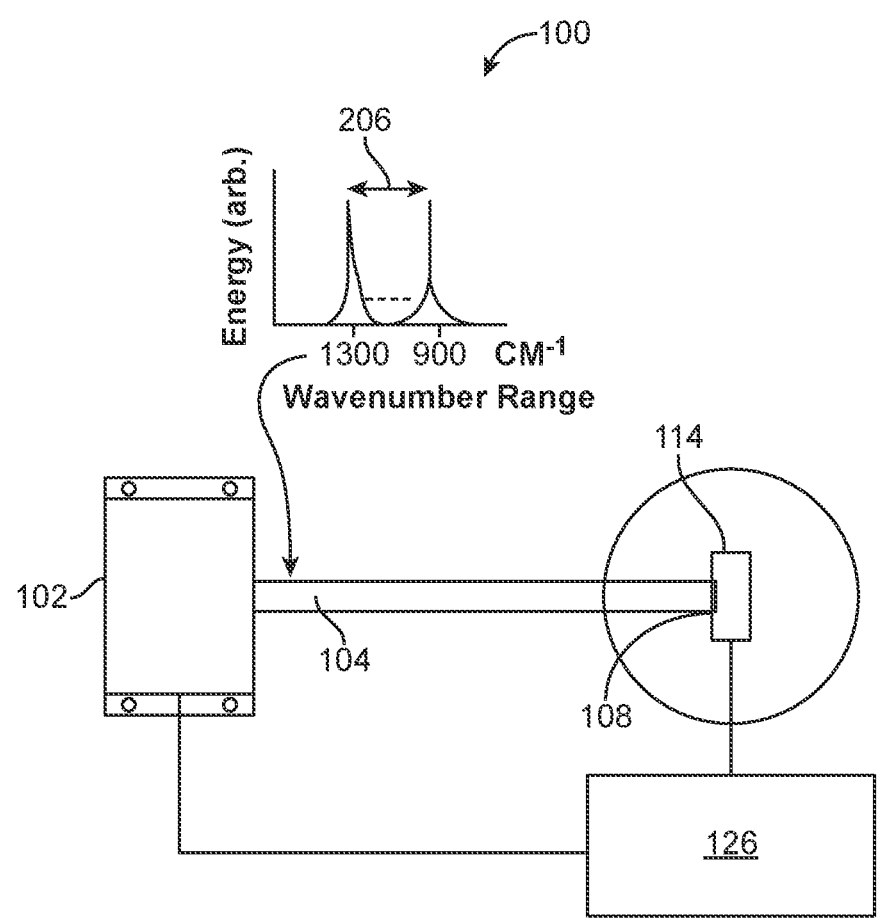
FIG. 4A shows an apparatus to measure a plurality of spectra of a sample with a tunable laser in accordance with embodiments.

FIG. 4A shows an apparatus 100 to measure a plurality of spectra of a sample 108 with a tunable laser 102 in accordance with embodiments. The tunable laser can be used to measure an infra-red absorbance profile of the sample in one or more of many ways as described herein. The apparatus of FIG. 4A may comprise one or more components of the apparatus as described herein. The laser and sensor 114 can be coupled to a processor 126 as described herein. The tunable laser may comprise one or more of many known tunable lasers. The tunable laser may emit a substantially collimated laser beam as described herein. The substantially collimated laser beam may have a cross-sectional diameter within a range from about 2-10 millimeters, for example. The sample may comprise a sample placed on a substrate, such as a substrate transparent to the infrared light, for example.

In many embodiments, the tunable laser comprises a tunable external cavity quantum cascade laser (hereinafter "QCL"). The tunable laser can be tuned to one or more of many wavelengths as described herein. In many embodiments, the tunable laser can be tuned to emit light in the mid-infrared portion of the electromagnetic spectra, for example within a range from about 4 to 11 microns. The laser can be tunable over a wavenumber range from about 900 to 1300 cm-1 (inverse centimeters), such that the laser has tunable range 206 of about 300 to 400 cm-1. The corresponding wavelengths can be within the range from about 4-11 um, for example. The bandwidth of the tunable laser can be about 1 cm-1 when tuned to a wavenumber, for example.

Figure 4B:
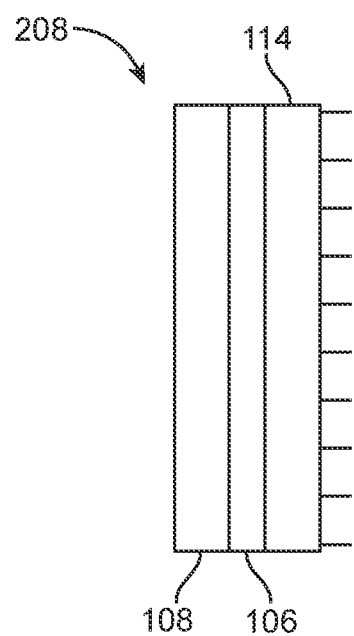
FIG. 4B shows the sensor array of FIG. 4A coupled to a sample.

FIG. 4B shows the sensor array 114 of FIG. 4A coupled to a sample 108. The sample can be coupled to the sensor array in one or more of many ways. For example, the sample can be configured in a sandwich configuration 208 with the sensor array. Alternatively, the sample can be imaged onto the sensor array as described herein. In many embodiments, the sample is coupled to the sensor array with a substrate support 106 such as a transparent plate. The sample and substrate can be placed on the sensor array. In many embodiments, the substrate is removable and may comprise a consumable component of the measurement apparatus, such that a new substrate can be provided with each sample.

In many embodiments, the area sensor array comprises components sensitive to mid infrared light energy as described herein. The mid-infrared sensor array may comprise a Mercury/Cadmium/Telluride (i.e. hereinafter "Hg/Cd/Te" or "MCT") detector comprising a plurality of pixels sensitive to light as described herein and known to a person of ordinary skill in the art. Alternatively or in combination, the mid-infrared sensor array may comprise a pyroelectric sensor array comprising a plurality of pyroelectric pixels sensitive to light as described herein. For example, pyroelectric sensor arrays are commercially available from Pyrosens and DIAS Infrared GMBH of Dresden, Germany and Dias Infrared Corp. of Warwick, N.Y. The pyroelectric array may comprise a lithium tantalate chip with 32, 64, 128, 256 or 510 rows and columns, for example, and additional elements can be provided by a person of ordinary skill in the art of conducting metal oxide semiconductor circuit design (hereinafter "CMOS") based on the disclosure provided herein. For example, a pyroelectric film can be placed on an area array CMOS sensor having MxN columns and rows as described herein to manufacture the area array sensor. The signals produced by the sensor elements can be processed in a CMOS circuit and coupled to a multiplexer coupled and circuitry coupled to the processor as described herein, for example.

While a tunable laser is shown, in some embodiments a wideband light source providing light as described herein can be combined with filters to measure the infrared absorbance profile, for example.

Figure 5:
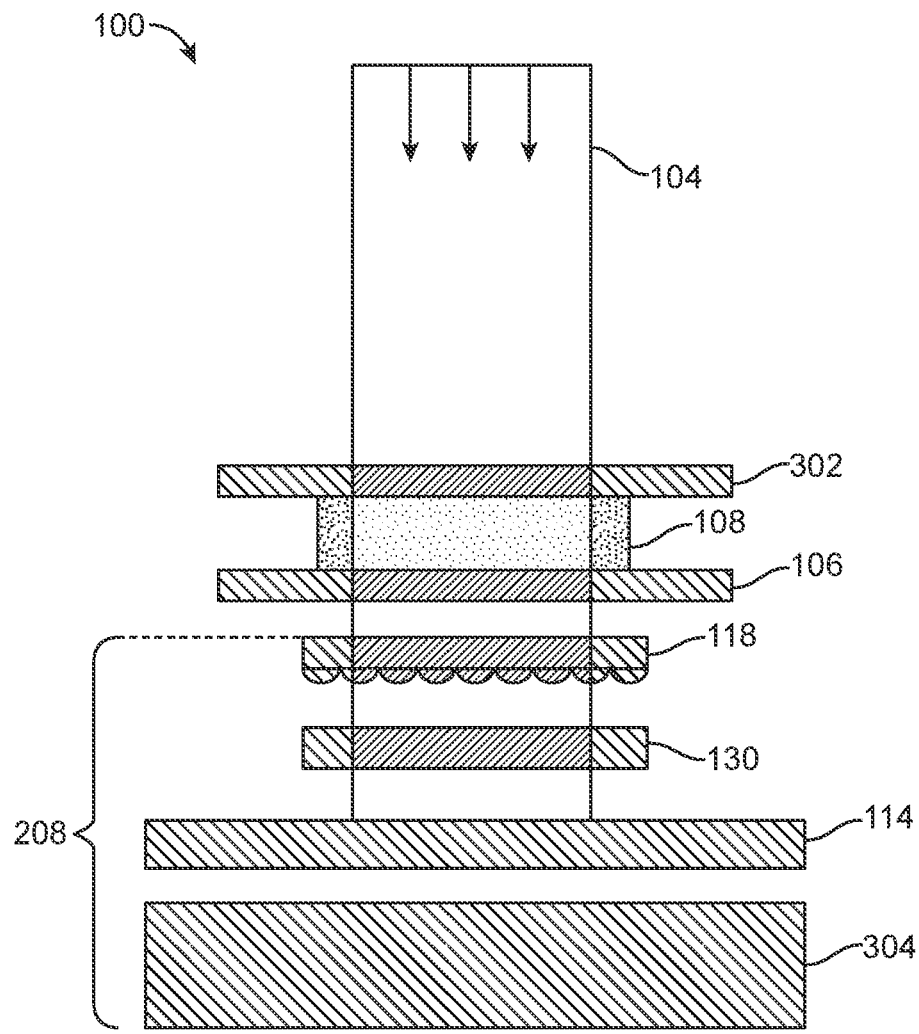
FIG. 5 shows a parallel optical computer using redundant array of detectors (hereinafter "RAD") for transmission mid-infrared sensor apparatus, in accordance with embodiments.

FIG. 5 shows a parallel optical computer 100 using redundant array of detectors (hereinafter "RAD") for transmission mid-infrared sensor apparatus. The apparatus comprises a laser source to generate a laser beam 104 and optics to direct the laser beam along an optical path as described herein. The laser beam can be, for example, a tunable QCL beam with a uniform cross section about 3-5 mm in diameter depending on the sensor area, having a tunable range of about 200 to 600 cm-1 and operating in a wavelength range of about 4-11 um. The laser beam is directed to the sample 108 and through a first optically transparent structure such as a cover slip 302 and a second optically transparent structure such as a substrate 106. The light energy transmitted through the sample can be measured to determine the transmission of the sample. The second optically transparent structure is coupled to a micro lens array 118 to improve light collection. An optical filter array 130 or LVF as described herein can receive light from the microlens array. The light transmitted through the optical filter is received by a pyroelectric area sensor array 114 such as a pyroelectric megapixel sensor array. The pyroelectric sensor array is coupled to a CMOS readout device 304 such as CMOS two dimensional readout device. One or more of the microlens array, the optical filter array, the LVF, pyroelectric megapixel sensor array, or the CMOS readout device can be configured in a sandwich configuration 208, for example. The substrate may comprise a flat plate such as a microscope slide configured to be placed on the microlens array, for example.

One or more of microlens array, the optical filter array, the LVF, pyroelectric megapixel sensor array, or the CMOS readout device may each comprise layers on the sensor apparatus and can be configured in a sandwich configuration 208, without an air gap. Alternatively or in combination, an air gap can be provided between one or more of the layers. The lenslets of the lenslet array collect scatter in the forward direction and direct the scattered light toward the pyroelectric sensor.

Figure 6:
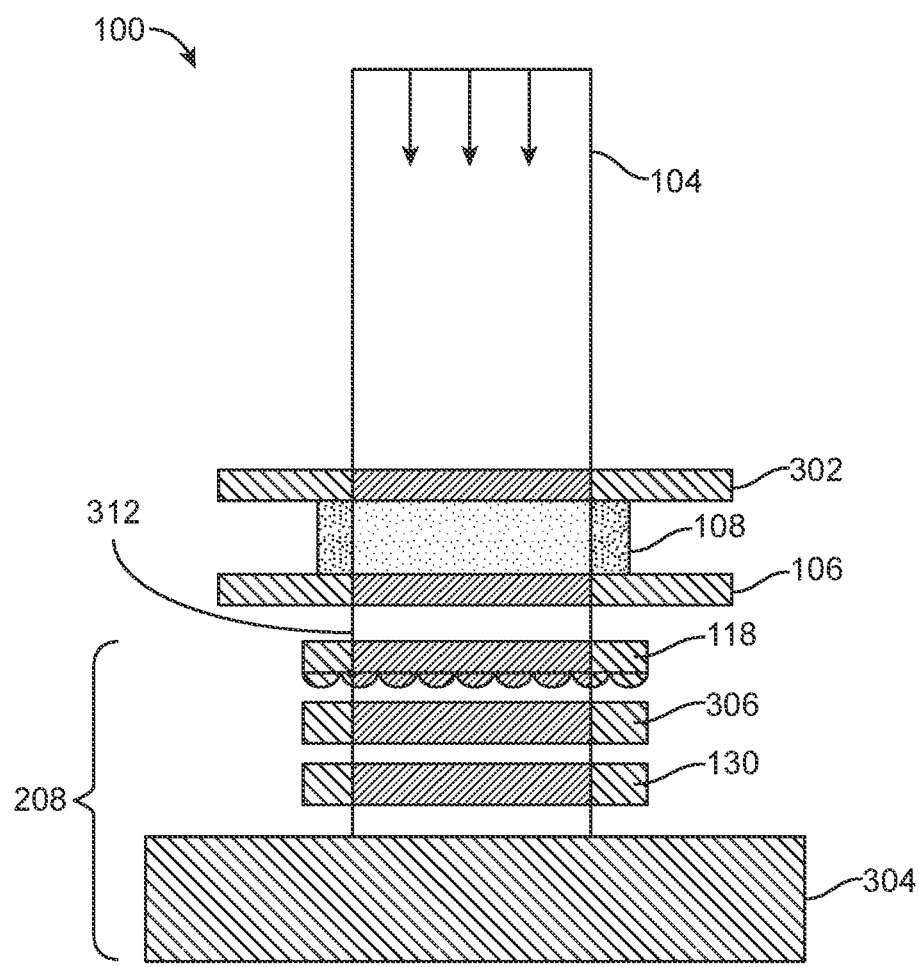
FIG. 6 shows a parallel optical computer using redundant array of detectors for a transmission Raman sensor apparatus, in accordance with embodiments.

FIG. 6 shows a parallel optical computer 100 using redundant array of detectors for a transmission Raman sensor apparatus. The apparatus comprises a laser source to generate a laser beam 104 and optics to direct the laser beam along an optical path as described herein. The laser beam can be, for example, a high power Raman laser beam with a uniform cross section about 3-5 mm in diameter depending on the sensor area. The laser beam is directed to the sample 108 and through a first optically transparent structure such as a cover slip 302 and a second optically transparent structure such as a substrate 106. The Raman forward scatter 312 transmitted through the sample can be measured to determine the transmission of the sample. The second optically transparent structure is coupled to a micro lens array 118 to improve light collection. A Raleigh rejection filter 306 receives light from the microlens array. An optical filter array 130 or LVF receives light from the Raleigh rejection filter. The optical filter array may comprise a plurality of Raman spectral selection filters, for example. One or more of the microlens array, the optical filter array, the Raleigh rejection filter, the LVF, pyroelectric megapixel sensor array, or the CMOS readout device 304 can be configured in a sandwich configuration 208, for example. The substrate may comprise a flat plate such as a microscope slide configured to be placed on the microlens array as described herein, for example. These components may comprise layers as described herein.

Figure 7:
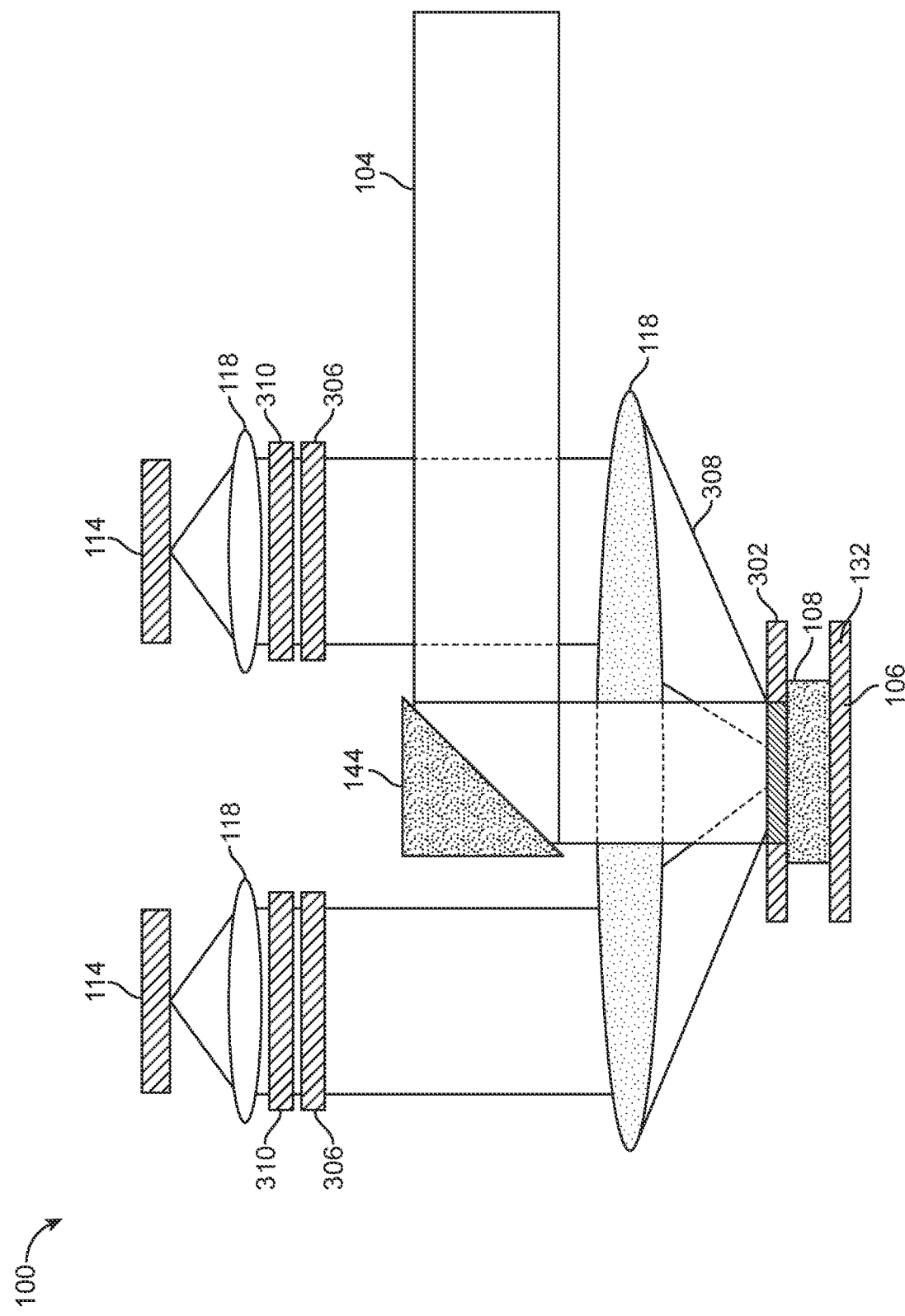
FIG. 7 shows a parallel optical computer using redundant array of detectors for a back scatter Raman sensor apparatus, in accordance with embodiments.

FIG. 7 shows a parallel optical computer 100 using redundant array of detectors for a back scatter Raman sensor apparatus. The laser beam 104 is directed toward the sample along an optical path as described herein. The laser beam can be, for example, a high power Raman laser beam with a uniform cross section about 3-5 mm in diameter depending on the sensor area. A mirror 144 may deflect the laser beam toward the sample 108. The beam is transmitted through an optically transparent cover slip 302 to the sample. The sample is supported on a substrate 106. An active heat sink 106 can be thermally coupled to the substrate 132.

Raman back scatter 308 is transmitted through the lens 118 and directed toward a plurality of sensor arrays 114. Light from the lens is transmitted to a plurality of Raleigh rejection filters (hereinafter "RRF") 306. Light from the Raleigh rejection filters is transmitted to a plurality of Raman spectral selection filters 310 hereinafter "RSSF"). Light from the plurality of Raman spectral selection filters is transmitted to a plurality of lenses. Light from the plurality of lens is transmitted to a plurality of area sensor arrays 114 (hereinafter "ASA"). In many embodiments, each sensor array is coupled to a lens of the plurality of lenses, an RSSF of the plurality of RSSFs, an RRF of the plurality of RRFs, for example. The plurality of area array sensors, the plurality of RSSFs, and the plurality of RRFs can be arranged radially around an axis of the laser beam extending toward the sample.

In many embodiments, the aperture of the collection lens is divided into a number of zones. In each of these zones a fixed Rayleigh rejection filter and a fixed spectral selection filter is provided. Instead of rotating a wheel, these substantially fixed embodiments have few or no moving parts. Each of the spectral filters can either select for a single wavelength or multiple wavelengths, in many embodiments based on those wavelengths that are most indicative of a specific chemical species. For example, a filter to select for glucose could have 10 pass bands at each of the 10 wavelengths that code for glucose. Alternatively, a filter for alcohol might have 5 pass bands at each of 5 wavelengths that code for alcohol. Each of the pass bands can be calibrated using known concentrations of analytes, for example.

Figure 8:
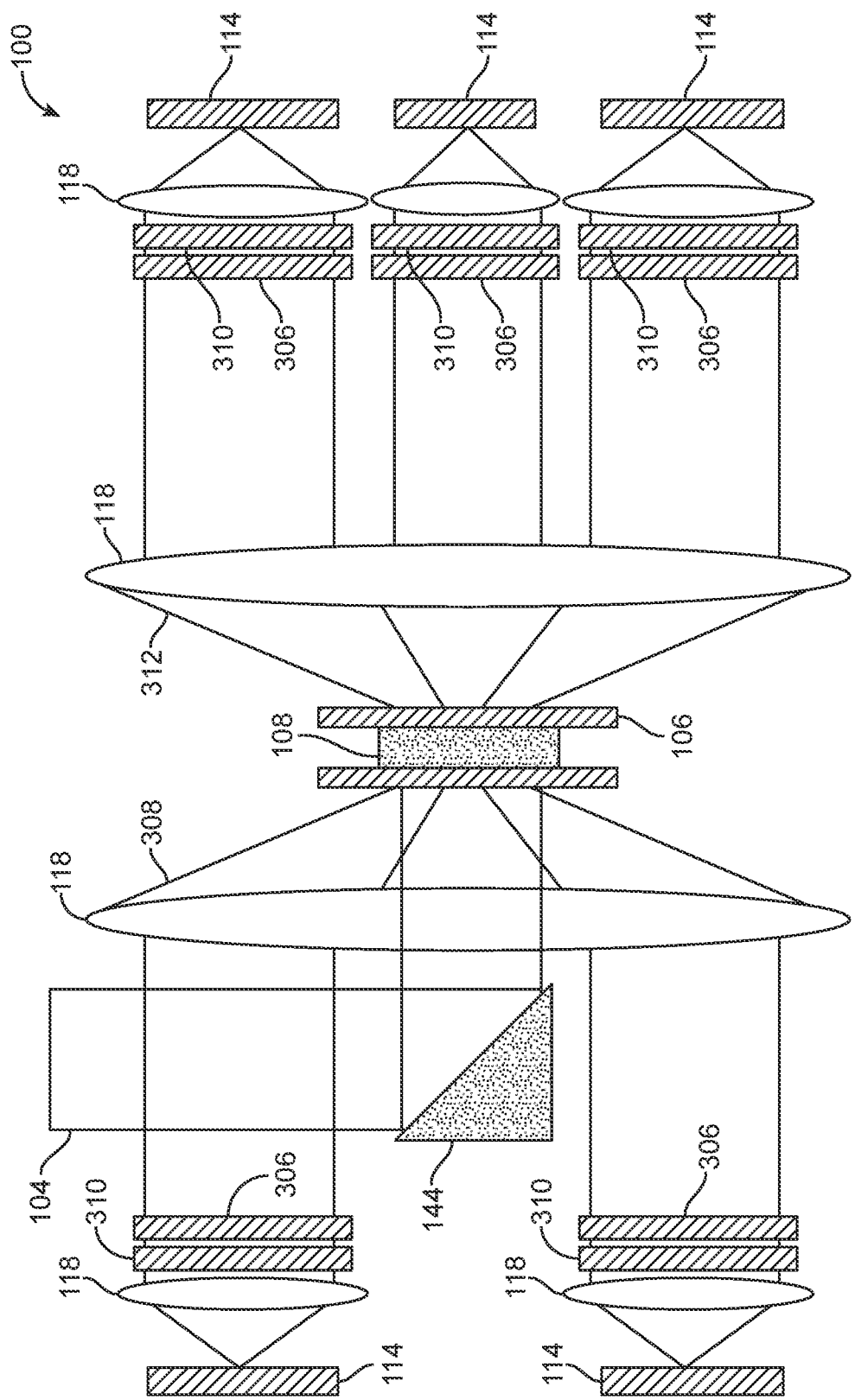
FIG. 8 shows a parallel optical computer using redundant array of detectors for a forward and back scatter Raman sensor apparatus, in accordance with embodiments.

FIG. 8 shows a parallel optical computer 100 using redundant array of detectors for a forward and back scatter Raman sensor apparatus. Raman back scatter 308 can be measured with one or more components of the apparatus 100 of FIG. 7, for example. The forward Raman scatter 312 can be measured with a plurality of detectors coupled to one or more of a plurality of lens 118, a plurality of RSSFs 310, or a plurality of RRFs 306, as described herein for example. The first substrate and the second substrate can be transparent as described herein in order to transmit light energy. The sample 108 can be configured in a sandwich configuration with substrates 106. In many embodiments, the sample is imaged as described herein onto the plurality of area sensor arrays 114.

As Raman scatter emits light in all directions these embodiments collect increased amounts of light over an increased solid angle, both in back-scatter and forward scatter mode. The Raman scatter can be emitted over a solid angle comprising of $4\pi$ steradians, and the embodiments collecting forward and back-scattered light can provide an improved sensitivity and signal to noise ration. In many embodiments, the forward scattered light and back scattered light are imaged from the sensor array onto the plurality of area array detectors.

The detectors and lenses can be arranged in one or more of many ways to collect light, and may be arranged in a generally spherical configuration or other configuration around the sample, for example, in order to collect scattered light.

One or more of curved mirrors or lenses as described herein placed in proximity to the sample and positioned to collect light from the sample and transmit the light to another optical component may comprise collectors configured to collect light. The collectors configured to collect light can transmit light to one or more imaging mirrors or lenses as described herein, for example.

EXAMPLES

The following examples are provided and are suitable for combination in accordance with embodiments disclosed herein. The examples are provided in accordance with embodiments and a person of ordinary skill in the art will recognize many alternatives and combinations. The examples can be combined with each other and embodiments as described herein in one or more of many ways, and may comprise steps, sub-steps, components or sub-components that can be added, replaced, removed, or combined, for example.

1a. Infrared spectroscopy while a blood sample is drying. Temporal dimension gives information about protein structure and changes. The sample can be heated to promote structure change. The sample can be heated in one or more of many ways such as mild heating to promote evaporation, intermediate heating, or heated in order to provide pyrolysis of the sample and analysis of the pyrolysate and gas phase.

1b. Stretch the blood spot on a substrate, get protein information. Drying while stretching. Polarization can be one or more of adjusted or measured.

2. Infrared spectroscopy while a sample is separating spatially on a substrate.

3. Linear Variable Filter (hereinafter "LVF") with a mask on top that trims the gain of the filter spectrally (optical computer).

4. An array of small round interference filter coatings in a rectangular grid array that can then be masked with a gain trimmer.

5. Lancing device that is a diamond knife that can be used as optical window for direct analysis of the blood sample, either in transmission or internal reflection mode.

6. Single cell Infrared for glucose measurement in a blood or fluid drop.

7. Flourescence monitor of ASA level for CV health.

8. Massively parallel optical computer for chemical detection. Individual channel infrared spectroscopy has detection limit near 1 PPM in a 1-minute measurement. Many blood analytes of interest have concentrations in the PPB range. In order to diagnose from a blood drop, an approach would be to use many instruments in parallel. Multiplex advantage as described herein builds with square root of the number of detectors. So to gain $10^3$ sensitivity requires $10^6$ parallel instruments, which are effectively optical computers of analyte concentration. 1 megapixel detectors ($10^6$ pixels) are already plentiful in the visible region, for example.

9. Near field transmission Raman spectroscopy. Sandwich a CMOS array detector together with a transmission blood cell and a collimated laser.

10. Massively parallel quantum optical computer for chemical detection.

Sample plane is sandwiched in detector near-field.
Use a sensor like used in the iPhone 5
Format is 1/3.2"
3264×2448 (8 MPixel)
4.54×3.42 mm sensor dimensions
1.4 micron pixel size
8 million pixels all parallel
Gives 2828× multiplex advantage
100 ppm nominal Raman sensitivity becomes 35 ppb
2 hour scan (as opposed to 1 minute) gives ~2 ppb Level of Detection (hereinafter "LOD")
Power density limit is 100 mW in 100 microns (per CDB)
Equivalent laser power can be 155 W
10. Large Area Parallel Detector (hereinafter "APD")
785 nm laser, collimated
large etendue optic for scatter collection, 1:1 imaging on APD
central obstruction for laser escape.
Alternative light source: broadband Quartz Tungsten Halogen (hereinafter "QTH") light source with grating to select wavelength.
Multiple band glucose analyte filter at Raman shift wavelengths
Sample positioning may comprise placing a blood drop on slide.
Massively parallel detector (e.g. iPhone camera sensor)
Analyte/Not Analyte filter in front of sensor (filter at detector peak sensitivity ~848 nm
Example filter is an 848 nm detector narrow band filter is 11787 cm-1
Raman shift of 950 cm-1 (glucose) may use a light source at 12737 cm-1 (785 cm-1)
11. A. Stationary interferometer hybrid optical computer
Detector 2D array. Each detector element has a filter in front of it, but not a bandpass filter. The filter would be a sine wave, each detector has a sine wave filter at a different frequency. The number of "channels" will determine the upper frequency (the Nyquist limit) and also the spectral resolution.
Broadband, large light source like a globar. The globar can be sandwiched with the detector and sample to make a very small instrument. The globar may comprise a silicon carbide rod that is electrically heated for use as a thermal light source.
The sample holder can be located between source and detector, for example sandwiched between the sample holder and the detector.
A scrambler mechanism can be provided to randomize the light. In many embodiments, detectors as described herein see the same portion of the sample.
11. B.
Instead of sine wave filters, each detector can have a patterned filter in front of it which is largely orthogonal to the other filters. In one case these filter profiles are random. In another embodiment they are set to the shape of the net analyte spectra or the pure component spectra.

Example 12. Deep UV Resonance Raman Spectrometer with Massively Parallel Optical Computer Limits of detection, in accordance with embodiments:
1 ng/dl
0.01 ng/ml
10 pg/ml
0.001 mcg/dl
Raman calculations
Excitation at 224=44643 cm-1
1000 cm-1 shift=229.13 nm
1016 cm-1 shift=229.21 nm
Approximate filter bandwidth=0.08 nm (0.03% of center wavelength, hereinafter "CWL")
2000 cm-1 shift=234.51 nm
Tuning range is 2% of CWL

Example 13. Near IR Raman Spectrometer with Massively Parallel Optical Computer Excitation at 785=12738 cm-1
1000 cm-1 shift=851.9 nm
1016 cm-1 shift=853.1 nm
Approximate filter bandwidth=1.2 nm
2000 cm-1 shift=931.3 nm
Tuning range is 9.4% of center wavelength (hereinafter "CWL")

Table 1 shows a list of metabolites suitable for measurement in accordance with embodiments described herein.

TABLE 1

| BIOMARKERS OF HEALTH/INFLAMMATION | |
|---|---|
| | (Serum/blood concentrations) |
| Glucose | 100 mg/dL |
| ATP | 1000 nanomol/L |
| | 507.18 ng/nanomol |
| | 507 ng/ml |
| GSH (glutathione) | 15-30 micromol/L |
| MT metallothionein | 1-10 ng/g in serum or urine |
| EPINEPHRINE | |
| Supine: | < or =111 pg/mL |
| Standing: | < or =141 pg/mL |
| NOREPINEPHRINE | |
| Supine: | 70-750 pg/mL |
| Standing: | 200-1,700 pg/mL |
| ACTH | 10-60 pg/mL |
| CORTISOL | 7-25 mcg/dL |
| Arginine Vasopressin Adults: | <1.7 pg/mL |
| Prolactin | |
| Males: | 3-13 ng/mL |
| Females: | 3-27 ng/mL |
| Cytokine panel | 0-5 pg/ml |
| TESTOSTERONE, TOTAL | 75-400 ng/dL |
| Progesterone Females, | 0.20-27.00 ng/mL |
| C-reactive protein | ≥150 mcg/dl |
| HEMATOLOGY | |
| Activated Partial Thromboplastin Time, Plasma | ≥150 sec (biomarker) |
| Fibrinogen | ≤60 - mg/dL |
| Hemoglobin >7 weeks | ≤6.0 ≥ 20.0 g/dL |
| INR (International Normalizing Ratio) - | ≥5.0 (biomarker) |
| CHEMISTRY | |
| Ammonia >1 year - | ≥500 mcg/dL |
| Calcium, Total | ≤6.5 ≥ 13.0 mg/dL |
| Calcium, Ionized, Blood | ≤3.0 ≥ 6.5 mg/dL |
| Carbon Monoxide (Carboxyhemoglobin Level) - | ≥20% |
| Creatinine, Blood/Plasma/Serum | ≥10.0 mg/dL |
| Creatine Kinase, Total - | ≥10,000 U/L |
| FT4 (Free Thyroxine) <50 yrs - | ≥9.0 ng/dL |
| FT4 (Free Thyroxine) ≥50 yrs - | ≥6.0 ng/dL |

TABLE 1-continued

BIOMARKERS OF HEALTH/INFLAMMATION

| | (Serum/blood concentrations) |
|---|---|
| Glucose, Plasma/Serum ≥4 weeks | ≤50 ≥ 400 mg/dL |
| Magnesium, Serum | ≤1.0 ≥ 9.0 mg/dL |
| Osmolality | ≤190 ≥ 390 mOsm/Kg |
| *pH (MCHS and AZ only) (biomarker) | <7.200 > 7.600 pH |
| *pC02, arterial (MCHS and AZ only) | <20.0 > 70.0 mmHg |
| *pO2 (MCHS) | <40.0 - mmHg |
| *pO2 (AZ) | ≤45.0 - mmHg |
| Phosphorus | ≤1.0 - mg/dL |
| Potassium (biomarker) | ≤2.5 ≥ 6.0 mmol/L |
| Sodium (biomarker) | ≤120 ≥ 160 mmol/L |

TOXICOLOGY/TDM

| | |
|---|---|
| Acetaminophen, S - | ≥120 mcg/mL |
| Acetone (Volatile Screen), | Any value detected mg/dL |
| Amitriptyline and Nortriptyline, S - | ≥300 ng/mL |
| Butalbital, S - | ≥10 mcg/mL |
| Caffeine, S - | ≥30 mcg/mL |
| Carbamazepine, Total, S - | ≥15.0 mcg/mL |
| Carbamazepine, Free, S - | ≥4.0 mcg/mL |
| Cyanide, B - | ≥2.0 mcg/mL |
| Desipramine, S - | ≥300 ng/mL |
| Digoxin, S - | ≥4.0 ng/mL |
| Disopyramide, S - | ≥7.0 mcg/mL |
| Doxepin and Nordoxepin, S | ≥300 ng/mL |
| Ethanol, Blood - | ≥400 mg/dL |
| Ethanol, Serum - | ≥400 mg/dL |
| Ethosuximide, S - | ≥101 mcg/mL |
| Ethylene Glycol, S - | ≥20 mg/dL |
| Imipramine and Desipramine, S - | ≥300 ng/mL |
| Isopropanol (Volatile Screen), | Any value detected mg/dL |
| Lidocaine, S - | >6.0 mcg/mL |
| Lead, Blood 0-15 yrs - | ≥20 mcg/dL |
| Lead, Blood ≥16 yrs - | ≥70 mcg/dL |
| Lithium, S - | >1.6 mmol/L |
| Methanol (Volatile Screen), | Any value detected mg/dL |
| Nortriptyline, S - | ≥300 ng/mL |
| Phenobarbital, S - | ≥60.0 mcg/mL |
| Phenytoin, Total, S - | ≥30.0 mcg/mL |
| Phenytoin, Free, S - | ≥2.5 mcg/mL |

Primidone and Phenobarbital, S

| | |
|---|---|
| Primidone | ≥15.0 mcg/mL |
| Phenobarbital | ≥60.0 mcg/mL |

Procainamide, S

| | |
|---|---|
| Procainamide | ≥10.0 mcg/mL |
| N-Acetylprocainamide | ≥40 mcg/mL |
| Quinidine, S - | ≥6.0 mcg/mL |
| Salicylates, S - | ≥50.0 mg/dL |
| Theophylline, S - | ≥20.0 mcg/mL |

Valproic Acid, Free and Total, S

| | |
|---|---|
| Free Valproic Acid | ≥15 mcg/mL |
| Total Valproic Acid | ≥120 mcg/mL |
| Valproic Acid, Total, S - | ≥120 mcg/mL |

VITAMIN DOSIMETRY

| | |
|---|---|
| Vitamin D | ≥20 ng/mL |

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. An apparatus to measure a blood sample, the apparatus comprising:
    a detector to measure a plurality of spatially and temporally resolved spectra of the blood sample;
    a light source to illuminate the detector with a light beam;
    a support to receive the blood sample and separate the blood sample; and
    a processor comprising a tangible medium, the processor coupled to the detector and the light source, the processor configured with instructions to illuminate the blood sample with a measurement beam and measure the plurality of spatially and temporally resolved spectra with the detector while the blood sample separates and to identify a component of the blood sample from the plurality of spatially and temporally resolved spectra.

2. The apparatus as in claim 1, wherein the light source comprises infrared light.

3. The apparatus as in claim 1, wherein the blood sample comprises one or more of an individual blood cell, a fluid of the blood sample, a hematocrit of the blood sample, or fluids of the hematocrit and the processor comprises instructions to measure the blood sample.

4. The apparatus as in claim 1, wherein the plurality of spectra comprises one or more of a plurality of Raman spectra or a plurality of infrared absorbance spectra.

5. The apparatus as in claim 1, wherein the detector comprises an area array detector.

6. The apparatus as in claim 5, further comprising:
    a plurality of optical filters located on a movable structure coupled to the processor to selectively position each of the plurality of optical filters along an optical path between the area array detector and the support, said each of the plurality of optical filters configured to transmit a range of wavelengths;
    wherein the light source comprises a tunable laser configured to emit a laser beam toward the detector; and
    wherein the processor comprises instructions to measure an amount of light energy emitted from the blood sample for said each of the plurality of optical filters.

7. The apparatus as in claim 1, wherein the support comprises an optically transmissive structure to analyze the blood sample.

8. The apparatus of claim 7, wherein the support is configured to measure transmission of the light beam through the blood sample.

9. The apparatus of claim 7, wherein the optically transmissive structure is configured to measure the blood sample with an internal reflection mode of the optically transmissive structure.

10. The apparatus as in claim 9, wherein the blood sample comprises blood cells located on a surface of the optically transmissive structure.

* * * * *